United States Patent
Furuho

(10) Patent No.: US 11,259,691 B2
(45) Date of Patent: Mar. 1, 2022

(54) BODY-INSERTABLE APPARATUS, TRANSMISSION METHOD, AND NON-TRANSITORY COMPUTER READABLE MEDIUM

(71) Applicant: OLYMPUS CORPORATION, Tokyo (JP)

(72) Inventor: Kazuya Furuho, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 627 days.

(21) Appl. No.: 16/210,079

(22) Filed: Dec. 5, 2018

(65) Prior Publication Data

US 2019/0110669 A1 Apr. 18, 2019

Related U.S. Application Data

(63) Continuation of application No. PCT/JP2017/007962, filed on Feb. 28, 2017.

(30) Foreign Application Priority Data

Jun. 20, 2016 (JP) .............................. JP2016-121861

(51) Int. Cl.
*A61B 1/04* (2006.01)
*A61B 1/045* (2006.01)
(Continued)

(52) U.S. Cl.
CPC ................ *A61B 1/041* (2013.01); *A61B 1/00* (2013.01); *A61B 1/00009* (2013.01);
(Continued)

(58) Field of Classification Search
CPC ....... A61B 1/041; A61B 1/00; A61B 1/00009; A61B 1/045; A61B 1/0638; A61B 1/0646
See application file for complete search history.

(56) References Cited

U.S. PATENT DOCUMENTS 8,315,471 B2 11/2012 Uchiyama et al.
8,503,743 B2 8/2013 Otsuka
(Continued)

FOREIGN PATENT DOCUMENTS

JP 2003070718 A 3/2003
JP 2005334080 A 12/2005
(Continued)

OTHER PUBLICATIONS

International Search Report dated May 16, 2017 issued in PCT/JP2017/007962.

*Primary Examiner* — Timothy J Neal
*Assistant Examiner* — William B Chou
(74) *Attorney, Agent, or Firm* — Scully, Scott, Murphy & Presser, P.C.

(57) ABSTRACT

A body-insertable apparatus includes an image sensor including a first pixel configured to receive light of a first wavelength band and to generate a first signal, a second pixel configured to receive light of a second wavelength band different from the first wavelength band and to generate a second signal, and a third pixel configured to receive a third wavelength band different from the first and second wavelength bands and to generate a third signal; and a processor comprising hardware, the processor being configured to allocate part of at least one of the first signal and the second signal to the third signal, when first light is received on the first and second pixels, the first light including at least one of the light of the first wavelength band and the light of the second wavelength band and excluding the light of the third wavelength band.

12 Claims, 10 Drawing Sheets

(51) Int. Cl.
   *A61B 1/06*         (2006.01)
   *A61B 1/00*         (2006.01)

(52) U.S. Cl.
   CPC ............ *A61B 1/045* (2013.01); *A61B 1/0638* (2013.01); *A61B 1/0646* (2013.01)

(56) References Cited

U.S. PATENT DOCUMENTS

| | | | |
|---|---|---|---|
| 10,631,720 B2 * | 4/2020 | Igarashi | ............ A61B 1/00045 |
| 2002/0183592 A1 | 12/2002 | Suzuki et al. | |
| 2017/0258304 A1 | 9/2017 | Ioka et al. | |

FOREIGN PATENT DOCUMENTS

| | | | |
|---|---|---|---|
| JP | 2006166940 A | 6/2006 | |
| JP | 2006198106 A | 8/2006 | |
| JP | 2009232218 A | 10/2009 | |
| JP | 2010169596 A | 8/2010 | |
| JP | 2012231377 A | 11/2012 | |
| JP | 2013162340 A | 8/2013 | |
| JP | 2016055052 A | 4/2016 | |
| WO | 2016088269 A1 | 6/2016 | |

\* cited by examiner

FIG.5A
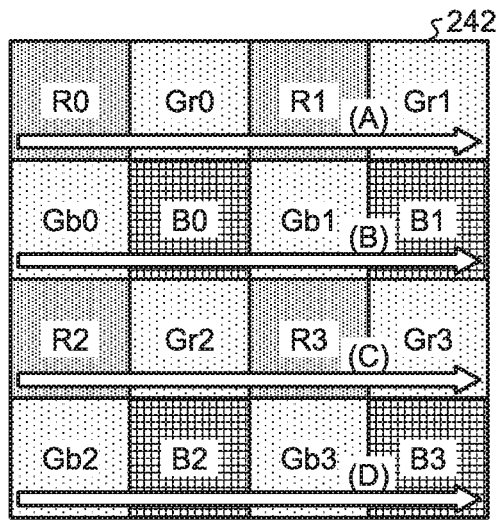
FIG.5B
| R0 | Gr0 | R1 | Gr1 | Gb0 | B0 | Gb1 | B1 | R2 | Gr2 | R3 | Gr3 | Gb2 | B2 | Gb3 | B3 |
|---|---|---|---|---|---|---|---|---|---|---|---|---|---|---|---|
| 12 bits | 12 bits | 12 bits | 12 bits | 12 bits | 12 bits | 12 bits | 12 bits | 12 bits | 12 bits | 12 bits | 12 bits | 12 bits | 12 bits | 12 bits | 12 bits |
FIG.5C
| R0 | Gr0 | R1 | Gr1 | Gb0 | B0 | Gb1 | B1 | R2 | Gr2 | R3 | Gr3 | Gb2 | B2 | Gb3 | B3 |
|---|---|---|---|---|---|---|---|---|---|---|---|---|---|---|---|
| 8 bits | 8 bits | 8 bits | 8 bits | 8 bits | 8 bits | 8 bits | 8 bits | 8 bits | 8 bits | 8 bits | 8 bits | 8 bits | 8 bits | 8 bits | 8 bits |
FIG.5D
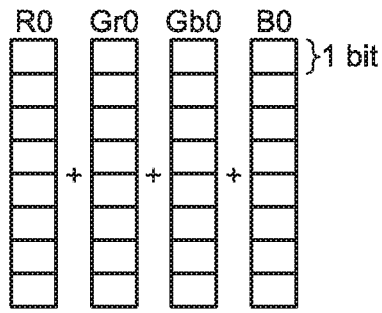

| R0 | Gr0 | R1 | Gr1 | Gb0 | B0 | Gb1 | B1 | R2 | Gr2 | R3 | Gr3 | Gb2 | B2 | Gb3 | B3 |
|---|---|---|---|---|---|---|---|---|---|---|---|---|---|---|---|
| 12 bits | 12 bits | 12 bits | 12 bits | 12 bits | 12 bits | 12 bits | 12 bits | 12 bits | 12 bits | 12 bits | 12 bits | 12 bits | 12 bits | 12 bits | 12 bits |

| R0 | Gr0 | R1 | Gr1 | Gb0 | B0 | Gb1 | B1 | R2 | Gr2 | R3 | Gr3 | Gb2 | B2 | Gb3 | B3 |
|---|---|---|---|---|---|---|---|---|---|---|---|---|---|---|---|
| Gr0 2 bits Gb0 2 bits B0 4 bits | 8 bits | Gr1 2 bits Gb1 2 bits B1 4 bits | 8 bits | 8 bits | 8 bits | 8 bits | 8 bits | Gr2 2 bits Gb2 2 bits B2 4 bits | 8 bits | Gr3 2 bits Gb3 2 bits B3 4 bits | 8 bits | 8 bits | 8 bits | 8 bits | 8 bits |

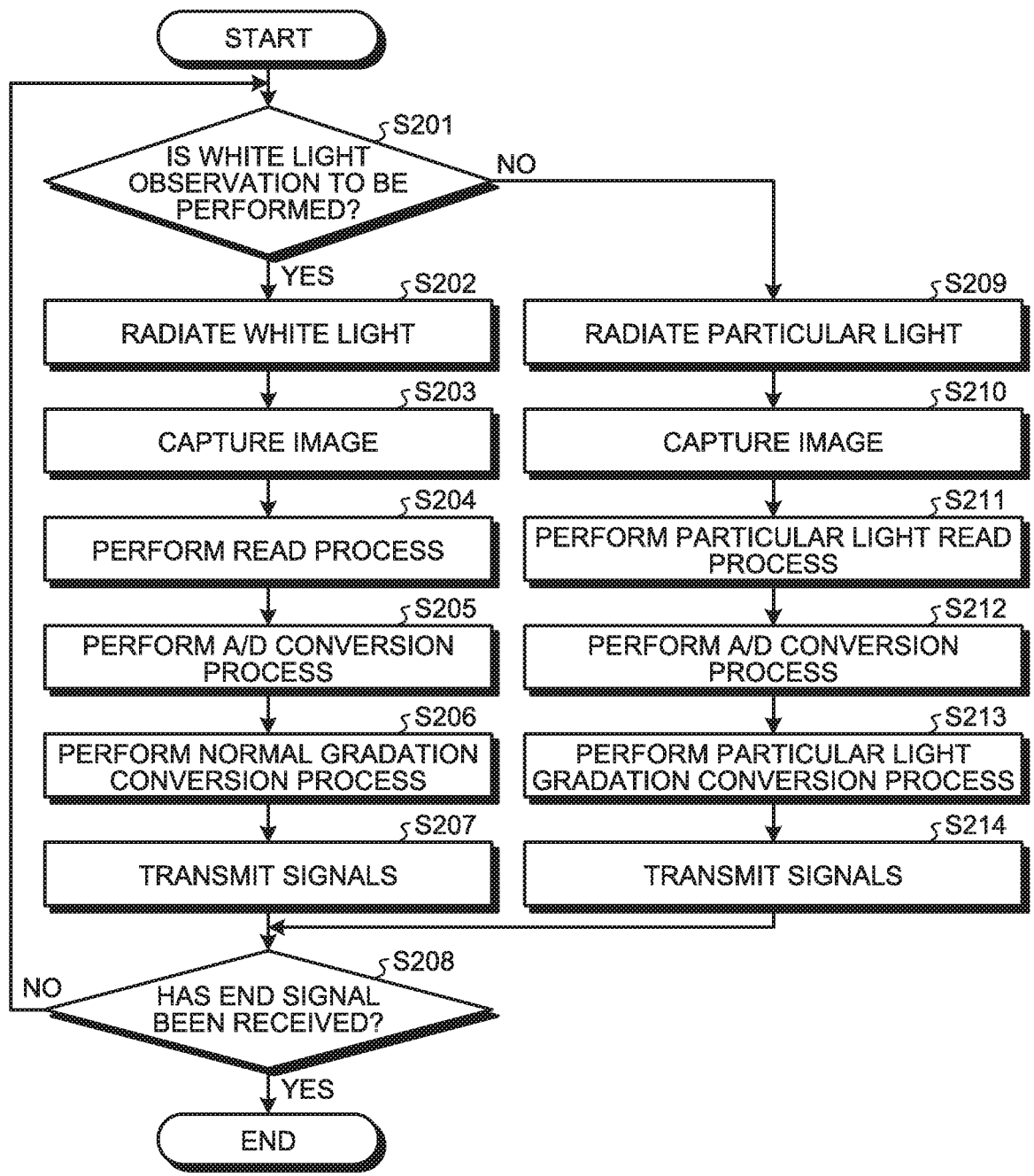

FIG.9A

| Gr0 | Gr1 | Gb0 | B0 | Gb1 | B1 | Gr2 | Gr3 | Gb2 | B2 | Gb3 | B3 |
|---|---|---|---|---|---|---|---|---|---|---|---|
| 12 bits | 12 bits | 12 bits | 12 bits | 12 bits | 12 bits | 12 bits | 12 bits | 12 bits | 12 bits | 12 bits | 12 bits |

FIG.9B

| Gr0 | Gr1 | Gb0 | B0 | Gb1 | B1 | Gr2 | Gr3 | Gb2 | B2 | Gb3 | B3 |
|---|---|---|---|---|---|---|---|---|---|---|---|
| 10 bits | 10 bits | 10 bits | 12 bits | 10 bits | 12 bits | 10 bits | 10 bits | 10 bits | 12 bits | 10 bits | 12 bits |

FIG.10

| Gr0 | Gr1 | Gb0 | B0 | Gb1 | B1 | Gr2 | Gr3 | Gb2 | B2 | Gb3 | B3 |
|---|---|---|---|---|---|---|---|---|---|---|---|
| 10 bits | 10 bits | 10 bits | 10 bits | 10 bits | 10 bits | 10 bits | 10 bits | 10 bits | 10 bits | 10 bits | 10 bits |

BODY-INSERTABLE APPARATUS, TRANSMISSION METHOD, AND NON-TRANSITORY COMPUTER READABLE MEDIUM

CROSS-REFERENCE TO RELATED APPLICATION

This application is a continuation of PCT International Application No. PCT/JP2017/007962 filed on Feb. 28, 2017 which claims the benefit of priority from Japanese Patent Application No. 2016-121861, filed on Jun. 20, 2016, the entire contents of which are incorporated herein by reference.

BACKGROUND

The present disclosure relates to a body-insertable apparatus that allows for observation of a subject to be observed, a transmission method, and a non-transitory computer readable medium.

In recent years, there has been a known endoscope capable of acquiring a narrow band light image and a white light image in each of which a capillary blood vessel on the surface layer of a mucous membrane and a fine pattern of the mucous membrane can be observed by irradiating biological tissue with white light or narrow band light and capturing the images by an imaging unit (see Japanese Laid-open Patent Publication No. 2006-198106).

SUMMARY

The present disclosure is directed to an improvement in a body-insertable apparatus, a signal transmission method for the body-insertable apparatus, and a non-transitory computer readable medium.

According to a first aspect of the present disclosure, a body-insertable apparatus is provided which an image sensor including a first pixel configured to receive light of a first wavelength band and to generate a first image signal, a second pixel configured to receive light of a second wavelength band that is different from the first wavelength band and to generate a second image signal, and a third pixel configured to receive a third wavelength band that is different from the first wavelength band and the second wavelength band and to generate a third image signal; and a processor comprising hardware, wherein the processor is configured to allocate a part of at least one of the first image signal and the second image signal to the third image signal, when first light is received on the first pixel and the second pixel, the first light including at least one of the light of the first wavelength band and the light of the second wavelength band and excluding the light of the third wavelength band.

According to a second aspect of the present disclosure, there is provided a transmission method performed by a body-insertable apparatus including an image sensor having a first pixel configured to receive light of a first wavelength band and to generate a first image signal, a second pixel configured to receive light of a second wavelength band that is different from the first wavelength band and to generate a second image signal, and a third pixel configured to receive light of a third wavelength band that is different from the first wavelength band and the second wavelength band and to generate a third image signal, the transmission method including allocating a part of at least one of the first image signal and the second image signal to the third image signal, when first light is received on the first pixel and the second pixel, the first light including at least one of the light of the first wavelength band and the light of the second wavelength band and excluding the light of the third wavelength band.

According to a third aspect of the present disclosure, there is provided a non-transitory computer readable medium storing a program that causes a body-insertable apparatus including an image sensor having a first pixel configured to receive light of a first wavelength band and to generate a first image signal, a second pixel configured to receive light of a second wavelength band that is different from the first wavelength band and to generate a second image signal, and a third pixel configured to receive light of a third wavelength band that is different from the first wavelength band and the second wavelength band and to generate a third image signal, to execute a process including allocating a part of at least one of the first image signal and the second image signal to the third image signal, when first light is received on the first pixel and the second pixel, the first light including at least one of the light of the first wavelength band and the light of the second wavelength band and excluding the light of the third wavelength band.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 5A is a diagram schematically illustrating an outline of a read process performed by an imaging unit in the capsule endoscope according to the first embodiment of the present disclosure;

FIG. 5B is a diagram schematically illustrating the number of bits of a digital image signal obtained by each of pixels after an A/D conversion process is performed by an A/D converter in the capsule endoscope according to the first embodiment of the present disclosure;

FIG. 5C is a diagram schematically illustrating the number of bits of a digital image signal obtained by each of the pixels after a gradation conversion process is performed by a gradation converter in the capsule endoscope according to the first embodiment of the present disclosure;

FIG. 5D is a diagram schematically illustrating the number of bits of a digital image signal obtained by each of the pixels and transmitted by a transmitting/receiving unit in the capsule endoscope according to the first embodiment of the present disclosure;

FIG. 7 is a flowchart illustrating an outline of a process performed by a capsule endoscope according to a second embodiment of the present disclosure;

FIG. 9A is a diagram schematically illustrating the number of bits of a digital image signal obtained by each of the pixels before an A/D conversion process is performed by an A/D converter in the capsule endoscope according to the second embodiment of the present disclosure;

FIG. 9B is a diagram schematically illustrating the number of bits of a digital image signal obtained by each of the pixels after the particular light gradation conversion process performed is by a gradation converter in the capsule endoscope according to the second embodiment of the present disclosure; and FIG. 10 is a diagram schematically illustrating the number of bits of a digital image signal obtained by each of the pixels before the particular light gradation conversion process performed is by the gradation converter in the capsule endoscope according to the second embodiment of the present disclosure.

DETAILED DESCRIPTION OF THE PREFERRED EMBODIMENTS

Figure 1:
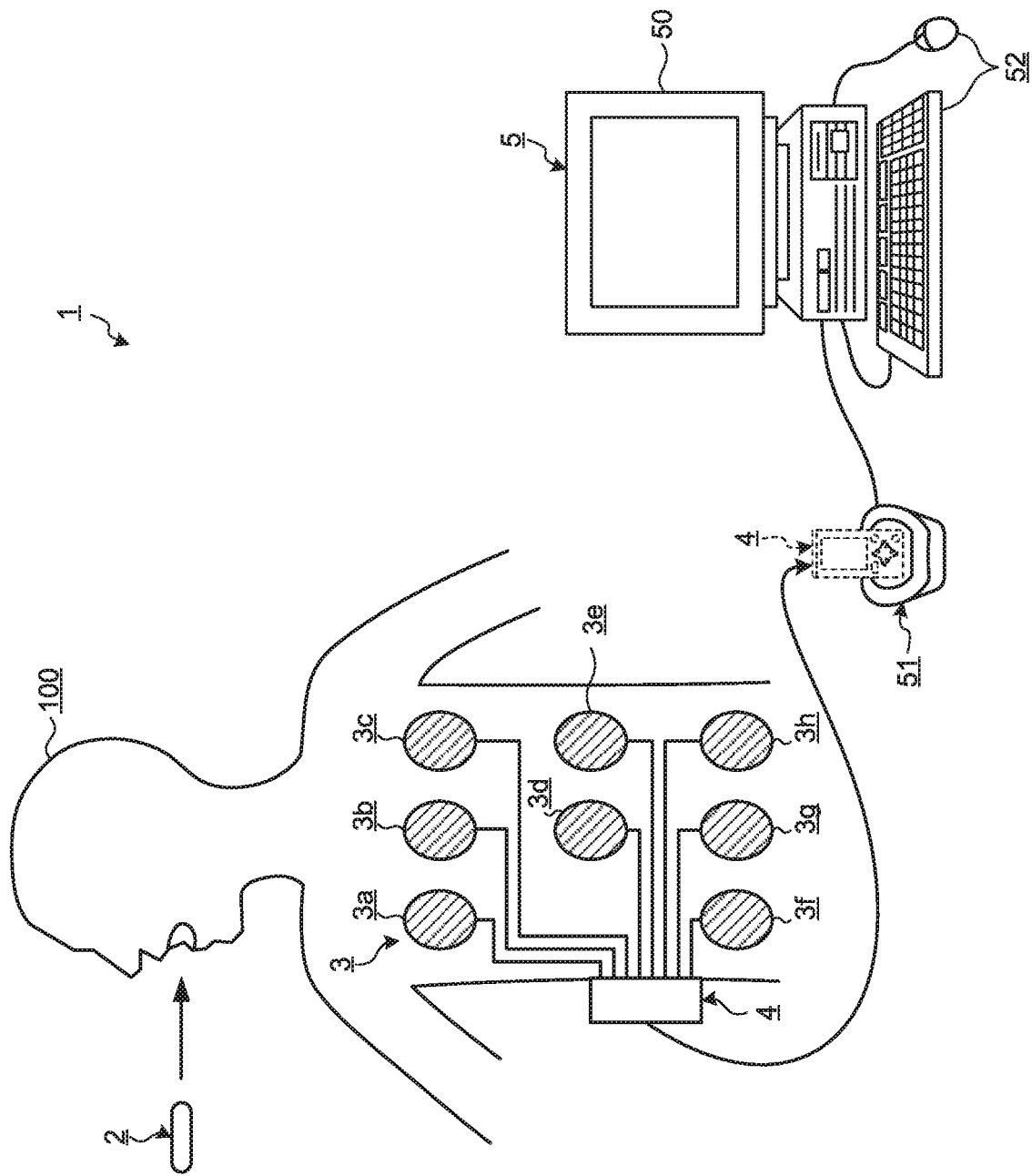
FIG. 1 is a schematic diagram illustrating a configuration of a capsule endoscope system according to a first embodiment of the present disclosure.

In the following, modes for carrying out the present disclosure will be described in detail with reference to the accompanying drawings. However, the present disclosure is not limited to the embodiments described below. Furthermore, in the drawings used for the following description, shapes, sizes, and positional relationships are only schematically illustrated so that the content of the present disclosure can be understood. Namely, the present disclosure is not limited to only the shapes, the sizes, and the positional relationships illustrated in the drawings. Furthermore, in a description below, a description will be given of, as an example, a capsule endoscope system that includes a processing device that receives a radio signal from a capture capsule endoscope, which is introduced into a subject and captures an in-vivo image of the subject, and that displays the in-vivo image of the subject; however, the present disclosure is not limited to the embodiments. Furthermore, components that are identical to those in embodiments are assigned the same reference numerals.

First Embodiment

Configuration of the capsule endoscope system FIG. 1 is a schematic diagram illustrating a capsule endoscope system according to a first embodiment of the present disclosure.

A capsule endoscope system 1 illustrated in FIG. 1 includes a capsule endoscope 2 that captures an in-vivo image inside a subject 100; a receiving antenna unit 3 that receives a radio signal transmitted from the capsule endoscope 2 that is introduced into the subject 100; a receiving device 4 in which the receiving antenna unit 3 is connected so as to be freely inserted to and removed from the receiving device 4 and that performs a predetermined process on the radio signal received by the receiving antenna unit 3 and records or displays the result; and an image processing apparatus 5 that processes and/or displays an image associated with an image signal inside the subject 100 captured by the capsule endoscope 2.

The capsule endoscope 2 has an image capturing function for capturing inside the subject 100 and a radio communication function for transmitting in-vivo information including the image signal obtained by capturing an image inside the subject 100 to the receiving antenna unit 3. The capsule endoscope 2 is swallowed into the subject 100, passes through an esophagus of the subject 100, and moves inside the body cavity of the subject 100 by a peristaltic movement of a lumen of a digestive tract. The capsule endoscope 2 sequentially captures images inside the body cavity of the subject 100 at short time intervals of, for example, 0.5 seconds (2 fps) while moving inside the body cavity of the subject 100, generates an image signal of the captured image inside the subject 100, and sequentially and wirelessly transmits the image signals to the receiving antenna unit 3. Furthermore, a configuration of the capsule endoscope 2 will be described in detail later.

The receiving antenna unit 3 includes receiving antennas 3a, 3b, 3c, 3d, 3e, 3f, 3g, and 3h. Each of the receiving antennas 3a to 3h receives a radio signal from the capsule endoscope 2 and transmits the radio signal to the receiving device 4. The receiving antennas 3a to 3h are formed by using loop antennas. Each of the receiving antennas 3a to 3h is attached to a predetermined position on an outer surface of the body of the subject 100, such as a position associated with each of the organs that are present inside the subject 100 and that corresponds to the passing route of the capsule endoscope 2.

The receiving device 4 records an image signal inside the subject 100 included in a radio signal received from the capsule endoscope 2 via the receiving antennas 3a to 3h. Or the receiving device 4 may display an image based on an image signal acquired inside the subject 100. The receiving device 4 records positional information, time information, and the like of the capsule endoscope 2 by associating the information with the radio signal received via the receiving antennas 3a to 3h. The receiving device 4 is carried by the subject 100 by being stored in a receiving device holder (not illustrated) during the period of time for which an examination using the capsule endoscope 2 is performed, such as the period of time for which the capsule endoscope 2 is introduced from the mouth of, for example, the subject 100, passes through a digestive tract, and is discharged from the subject 100. After the end of the examination performed by using the capsule endoscope 2, the receiving device 4 is removed from the subject 100 and is connected to the image processing apparatus 5 in order to transfer the image signals or the like received from the capsule endoscope 2.

The image processing apparatus 5 is constituted by using a computer, a mobile terminal, or the like and includes a display device 50 that displays an image associated with an image signal acquired inside the subject 100 and transferred from the receiving device 4; a cradle 51 that reads an image signal or the like from the receiving device 4; and an operation input device 52, such as a keyboard or a mouse. The display device 50 is constituted by using a display panel, such as a liquid crystal display panel or an organic electro luminescence (EL) display panel. The cradle 51 transfers, to the image processing apparatus 5 when the receiving device 4 is attached, an image signal from the receiving device 4 and correlation information, such as, positional information, time information, and identification information on the capsule endoscope 2 that are correlated with this image signal. The operation input device 52 inputs an operation performed by a user to a computer. While operating the operation input device 52 and viewing images inside the subject 100 that are sequentially displayed by the image processing apparatus 5, the user observes a living body region, such as an esophagus, a stomach, a small intestine, and a large intestine, inside the subject 100 and diagnoses the subject 100.

Configuration of the Capsule Endoscope

Figure 2:
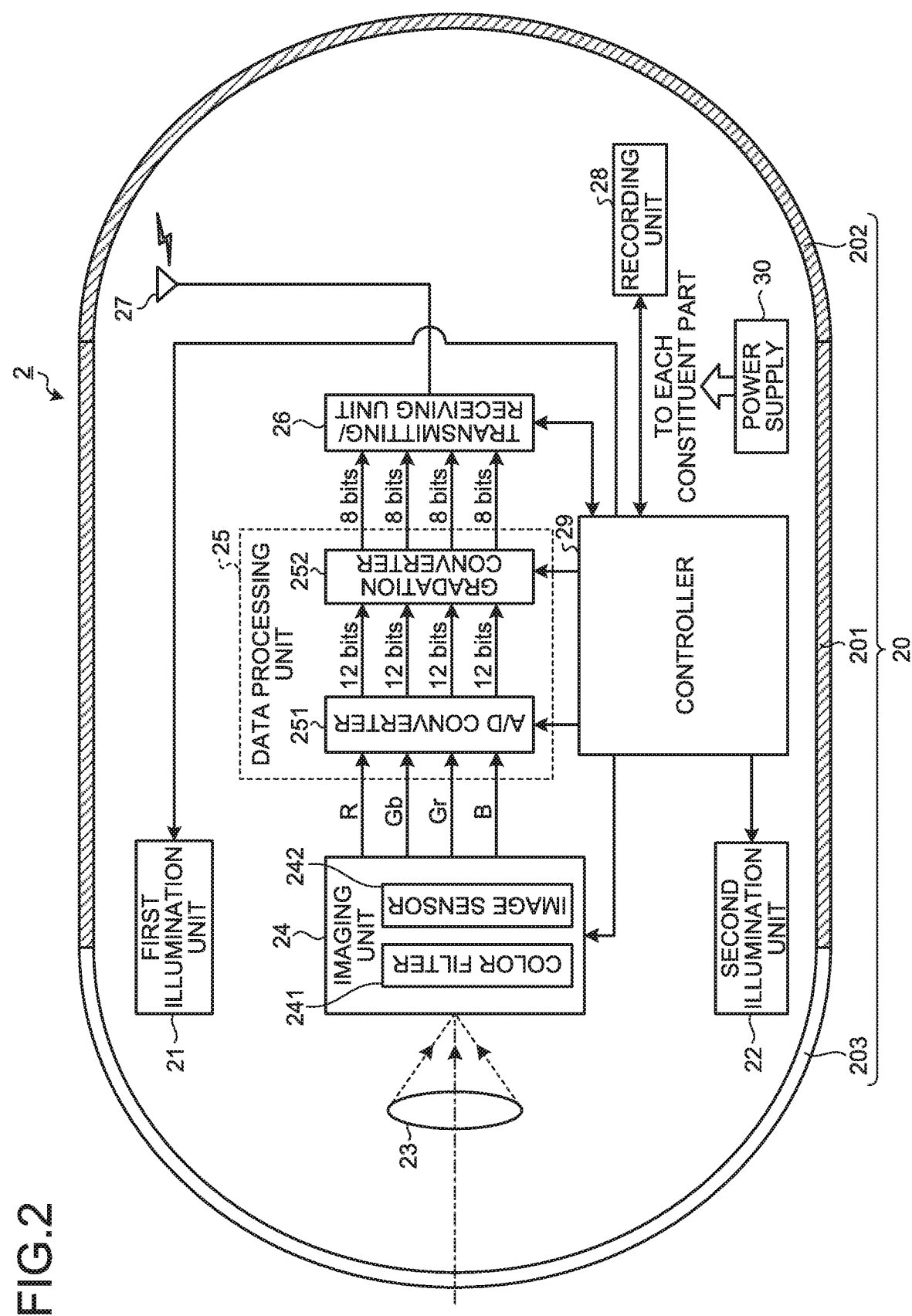
FIG. 2 is a block diagram illustrating a functional configuration of a capsule endoscope according to the first embodiment of the present disclosure.

In the following, a configuration of the capsule endoscope 2 will be described in detail. FIG. 2 is a block diagram illustrating a functional configuration of the capsule endoscope 2.

The capsule endoscope 2 illustrated in FIG. 2 includes a capsule-shaped casing 20 having a shape that can be easily introduced into a digestive tract of the subject; a first illumination unit 21 that irradiates the field of view of the capsule endoscope 2 with white light; a second illumination unit 22 that irradiates the field of view of the capsule endoscope 2 with particular light; an optical system 23 that forms an object image; an imaging unit 24 that receives the object image formed by the optical system 23, and performs photoelectric conversion on the object image, thereby generate an image signal; a data processing unit 25 that performs A/D conversion on the analog image signal generated by the imaging unit 24 thereby to generate a digital image signal, that converts gradation of a digital image signal to the number of predetermined bits (bit), and that outputs the digital image signal with the converted bit number; a transmitter/receiver 26 that transmits an image signal, which has been subjected to gradation conversion and has been input from the data processing unit 25, to the outside via an antenna 27 or that receives a radio signal sent from the outside via the antenna 27; a recording unit 28 that records various kinds of information on the capsule endoscope 2; a controller 29 that controls each of the component units in the capsule endoscope 2; and a power supply 30 that supplies electrical power to each of the component units in the capsule endoscope 2.

The capsule-shaped casing 20 is realized by covering both ends of the openings of a cylindrical casing 201 with dome-shaped casings 202 and 203. The dome-shaped casing 203 is formed by using a transparent member that can pass white light radiated by the first illumination unit 21 or particular light radiated by the second illumination unit 22. The capsule-shaped casing 20, which is formed by the cylindrical casing 201 and the dome-shaped casings 202 and 203, includes therein, as illustrated in FIG. 2, the first illumination unit 21, the second illumination unit 22, the optical system 23, the imaging unit 24, the data processing unit 25, the transmitter/receiver 26, the antenna 27, the recording unit 28, the controller 29, and the power supply 30.

The first illumination unit 21 radiates, under the control of the controller 29, white light toward an area including at least the field of view of the capsule endoscope 2 through the dome-shaped casing 203. The first illumination unit 21 is constituted by using a white light emitting diode (LED), or the like.

The second illumination unit 22 radiates, under the control of the controller 29, particular light toward an area including at least the field of view of the capsule endoscope 2 through the dome-shaped casing 203. The particular light mentioned here is light including light of a blue narrow band (for example, 390 nm to 445 nm) and light of a green narrow band (for example, 530 nm to 550 nm) used when the capsule endoscope 2 performs narrow band light observation (Narrow Band Imaging: NBI).

The optical system 23 condenses light reflected from a mucous membrane of the subject onto the imaging surface of the imaging unit 24 and forms an object image. The optical system 23 is formed by using one or more lenses, such as condenser lenses or focus lenses.

The imaging unit 24 sequentially generates, under the control of the controller 29 and in accordance with a predetermined frame rate, the image signals of the object image formed by the optical system 23 and outputs the generated image signals to the data processing unit 25. The imaging unit 24 includes a color filter 241 and an image sensor 242.

The color filter 241 passes light of a predetermined wavelength band. Specifically, the color filter 241 is constituted by a plurality of filters each of which passes light in a red wavelength band, light in a green wavelength band, and light in a blue wavelength band (for example, red: 600 nm to 700 nm, green: 500 nm to 600 nm, and blue: 400 nm to 500 nm).

Figure 3:
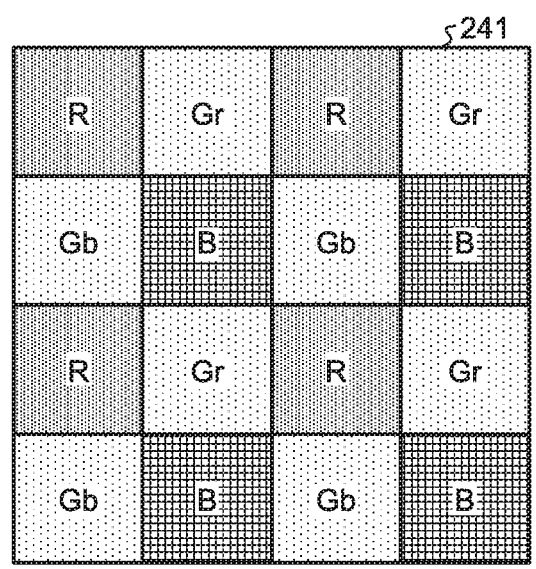
FIG. 3 is a schematic diagram illustrating a configuration of a color filter of the capsule endoscope according to the first embodiment of the present disclosure.

FIG. 3 is a schematic diagram illustrating a configuration of the color filter 241. As illustrated in FIG. 3, the color filter 241 is constituted by using filters R each of which passes light in a red wavelength band, filters Gr and filters Gb each of which passes light in a green wavelength band, and filters B each of which passes light in a blue wavelength band. Furthermore, in the color filter 241, each of the filters R, the filters Gr, the filters Gb, and the filters B is formed by being arranged on, based on Bayer arrangement, the light-receiving surface of corresponding pixels of the image sensor 242.

Referring back to FIG. 2, description is continuously given of the configuration of the capsule endoscope 2.

The image sensor 242 generates, under the control of the controller 29, an analog image signal by receiving, via the color filter 241, the object image formed by the optical system 23 and performing photoelectric conversion and then outputs the generated analog image signal to the data processing unit 25. The image sensor 242 is formed of a plurality of pixels that are arranged in a two-dimensional matrix and is constituted by using, for example, a complementary metal oxide semiconductor (CMOS) or a charge coupled device (CCD). In a description below, pixels formed by the R filters being arranged on the light-receiving surface are referred to as R pixels, pixels formed by the Gr filters being arranged on the light-receiving surface are referred to as Gr pixels, pixels formed by the Gb filters being arranged on the light-receiving surface are referred to as Gb pixels, and pixels formed by the B filters being arranged on the light-receiving surface is referred to as B pixels. Furthermore, a signal that is output from each of the plurality of B pixels is referred to as a first image signal, a signal that is output from each of the plurality of Gr pixels and the Gb pixels is referred to as a second image signal, and a signal that is output from each of the plurality of R pixels is referred to as a third image signal.

The data processing unit 25 includes an A/D converter 251 and a gradation converter 252. The data processing unit 25 performs, under the control of the controller 29, A/D conversion on the analog image signal generated by the imaging unit 24 and converts gradation of the digital image signal to a predetermined number of bits (bit).

The A/D converter 251, which may be constituted by using an ASIC, performs, under the control of the controller 29, an A/D conversion process of converting the analog image signal input from the imaging unit 24 to the digital image signal; and outputs the digital image signal to the gradation converter 252. Specifically, the A/D converter 251 converts the analog image signal that is input from each of the R pixels, the Gr pixels, the Gb pixels, and the B pixels in the image sensor 242 to the digital image signal with the predetermined number of bits and then outputs the digital image signal to the gradation converter 252. The number of predetermined bits mentioned here is 12 bits. Furthermore, the number of bits is not limited to this and may also appropriately be changed in accordance with the performance of the image sensor 242.

The gradation converter 252, which may be constituted by using an ASIC, converts, under the control of the controller 29, the digital image signal input from the A/D converter 251 to predetermined amount of data; and outputs the converted signal to the transmitter/receiver 26. Specifically, when the R pixels, the Gr pixels, the Gb pixels, and the B pixels receive white light, the gradation converter 252 performs the gradation conversion process of converting the 12-bit image signal of the first image signal, the second image signal, and the third image signal that are associated with the corresponding pixels and input from the A/D converter 251 to 8-bit image signal and resizing the amount of data. Then, the gradation converter 252 outputs the converted image signals to the transmitter/receiver 26. Furthermore, when the B pixel, the Gr pixel, and the Gb pixel receive particular light that includes at least one of a first wavelength band and a second wavelength band and that does not include a third wavelength band, the gradation converter 252 performs the gradation conversion process of allocating at least a part of one of the first image signal and the second image signal to the third image signal and then outputs the resultant signals to the transmitter/receiver 26.

Specifically, when the B pixel, the Gr pixel, and the Gb pixel receive the particular light, the gradation converter 252 performs the gradation conversion process of allocating a part of the first image signal to a first data area of the first image signal and allocating the rest of the first image signal to a third data area of the third image signal, and also allocating a part of the second image signal to a second data area of the second image signal and allocating the rest of the second image signal to the third data area of the third image signal. More specifically, the gradation converter 252 allocates an amount of data of each of the higher order bits of the first image signal and the second image signal to the first data area and the second data area, respectively, and allocating an amount of data of each of the lower order bits of the first image signal and the second image signal to the third data area allocated to the third image signal, and then outputs the resultant signals. For example, when the B pixel, the Gr pixel, and the Gb pixel receive the particular light, the gradation converter 252 allocates an amount of data of 8 bits of the higher order bits, out of 12 bits included in the first image signal, that is the same amount of data as the amount of data of the first data area to the first data area and allocating an amount of data of the lower order 4 bits that is the remaining amount of data of the first image signal to the third data area. Furthermore, the gradation converter 252 allocates an amount of data of 8 bits of the higher order bits, out of 12 bits included in the second image signal, that is the same amount of data as the amount of data of the second data area to the second data area and allocating an amount of data of the lower order 4 bits that is the remaining amount of data of the second image signal to the third data area. Incidentally, the gradation converter 252 may also output the image signal that has been subjected to gradation conversion to the recording unit 28 without outputting to the transmitter/receiver 26.

The transmitter/receiver 26 sequentially and wirelessly transmits the image signal that has been subjected to the gradation conversion and received from the gradation converter 252 to the outside via the antenna 27. Specifically, the transmitter/receiver 26 sequentially and wirelessly transmits the image signal that has been subjected to the gradation conversion and received from the gradation converter 252 to the outside via the antenna 27 at a rate of an amount of data per unit time defined based on the transmission band and the frame rate of imaging performed by the image sensor 242. Furthermore, the transmitter/receiver 26 may also generate a radio signal by performing signal processing, such as modulation, on the image signal that has been subjected to the gradation conversion, and transmit the resultant radio signal to the outside. Furthermore, the transmitter/receiver 26 receives the radio signal transmitted from the outside via the antenna 27, performs a decoding process or the like on the radio signal, and outputs the obtained radio signal to the controller 29.

The recording unit 28 is constituted by using a read only memory (ROM), a random access memory (RAM), or the like, and records various programs and the image signals executed by the capsule endoscope 2 and various kinds of information that is being processed by the capsule endoscope 2. Furthermore, the recording unit 28 may also sequentially record the image signals that have been subjected to the gradation conversion and received from the gradation converter 252 and collectively transmit the image signals that have been subjected to the gradation conversion to the outside after the capsule endoscope 2 is released to the outside of the body. Incidentally, the recording unit 28 may also perform signal processing, such as interpolation or compression, on the recorded image signals that have been subjected to the gradation conversion.

The controller 29 is constituted by using a central processing unit (CPU), or the like, performs control of driving each component in the capsule endoscope 2, and performs control of input/output of the signal between each of the components.

The power supply 30 is constituted by using a storage battery, such as a button type battery or a capacitor, and a switch that is switched by a command received from the controller 29. The power supply 30 supplies electrical power to each of the components in the capsule endoscope 2.

Process Performed by the Capsule Endoscope

Figure 4:
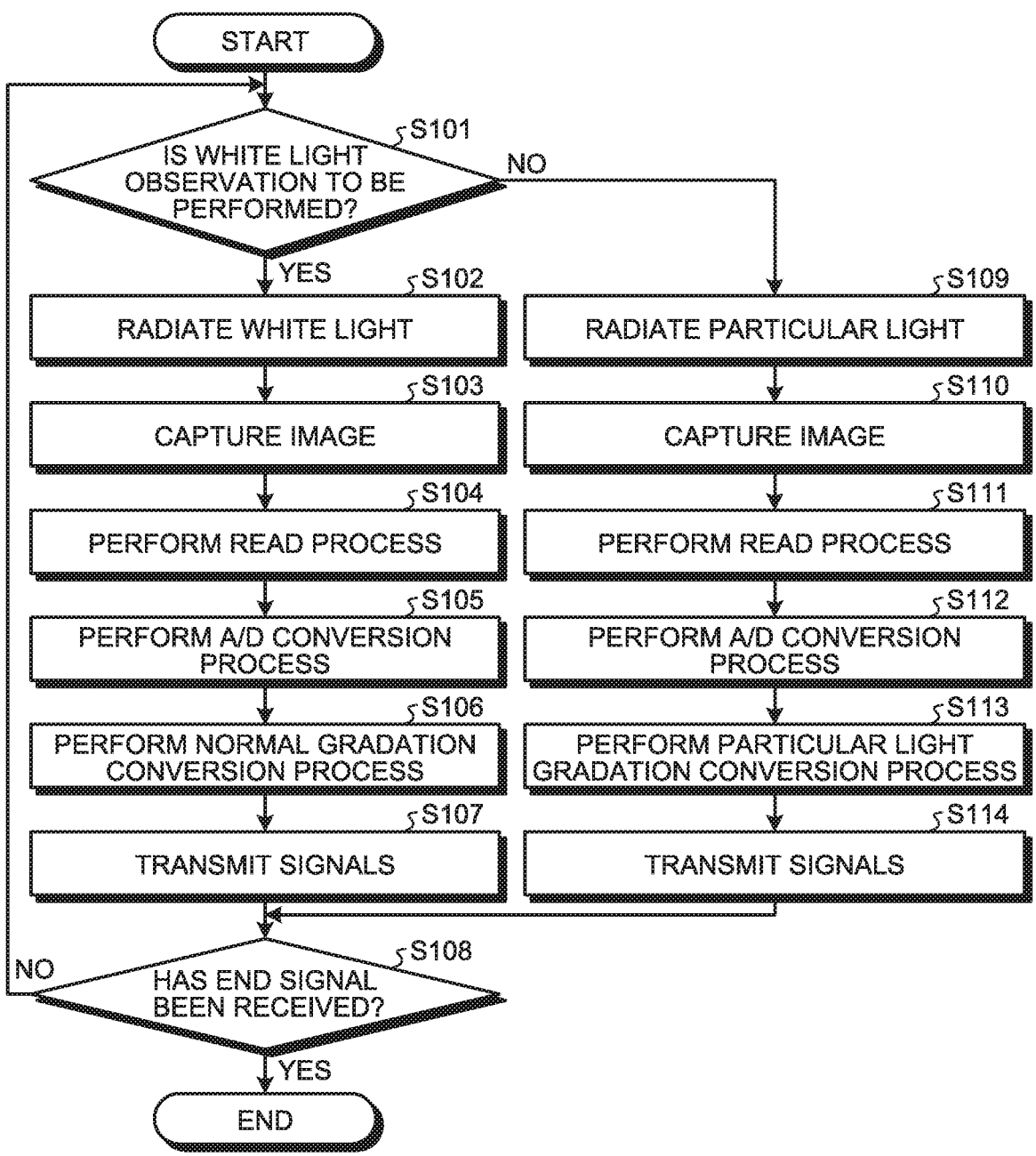
FIG. 4 is a flowchart illustrating an outline of a process performed by the capsule endoscope according to the first embodiment of the present disclosure.

In the following, the process performed by the capsule endoscope 2 will be described. FIG. 4 is a flowchart illustrating an outline of a process performed by the capsule endoscope 2. Incidentally, the processes described below may also be performed by using a method in which the controller 29 outputs an indication signal to each of the units in the capsule endoscope 2 and controls each of the units.

As illustrated in FIG. 4, first, a description will be given of a case in which an indication signal that indicates to perform white light observation has received from the outside via the antenna 27 and the transmitter/receiver 26 (Yes at Step S101). In this case, the first illumination unit 21 radiates white light (Step S102). Then, the imaging unit 24 captures an image of the area irradiated with the white light (Step S103).

Subsequently, the imaging unit 24 performs the read process of reading the image signal from each of the pixels in the image sensor 242 (Step S104).

Thereafter, the A/D converter 251 performs the A/D conversion process on the image signals that are read from the image sensor 242 (Step S105).

FIG. 5A is a diagram schematically illustrating an outline of a read process performed by the imaging unit 24. FIG. 5B is a diagram schematically illustrating the number of bits of a digital image signal obtained by each of the pixels after the A/D conversion process performed is by the A/D converter 251.

As illustrated in FIG. 5A, the imaging unit 24 reads an image signal from each of the pixels included in the image sensor 242 and outputs the read pixels (an arrow (A) to an arrow (B) to an arrow (C) to an arrow (D)). Then, the A/D converter 251 performs the A/D conversion process of converting the analog image signals, which have been output from the image sensor 242, to digital image signals. Consequently, the image signal from each of the pixels is converted to, as illustrated in FIG. 5B, the digital image signal with the predetermined number of bits, for example, 12 bits.

After the process at Step S105, the gradation converter 252 performs a normal gradation conversion process on the digital image signals output from the A/D converter 251 so as to be predetermined gradation (Step S106). Then, the transmitter/receiver 26 transmits the image signals subjected to the normal gradation conversion performed by the gradation converter 252 to the outside (Step S107). After the process at Step S107, the capsule endoscope 2 proceeds to Step S108 that will be described later.

FIG. 5C is a diagram schematically illustrating the number of bits of a digital image signal obtained by each of the pixels after the gradation conversion process performed is by the gradation converter 252. FIG. 5D is a diagram schematically illustrating the number of bits of each of a digital image signal obtained by the pixels, and transmitted by the transmitter/receiver 26. Furthermore, in FIG. 5D, 1 bit is schematically represented in a rectangular shape.

As illustrated in FIG. 5C, the gradation converter 252 performs the normal gradation conversion process on the 12-bit digital image signal input from the A/D converter 251 so as to be predetermined gradation. Specifically, as illustrated in FIG. 5C, an amount of data (8 bits) in each of the first, the second, and the third data areas allocated to the first, the second, and the third image signals, respectively, is smaller than the amount of data (12 bits) of each of the first, the second, and the third image signals. Consequently, the gradation converter 252 decreases the level of gradation by performing a resizing process decreasing the number of bits included in each of the image signals output from the pixels in an image associated with the digital image signal from 12 bits to 8 bits (from FIG. 5B to FIG. 5C). Then, as illustrated in FIG. 5D, the transmitter/receiver 26 outputs the image signal associated with each of the pixels (the R pixel, the Gr pixel, the Gb pixel, and the B pixel) with 8 bits subjected to the normal gradation conversion by the gradation converter 252.

After the process at Step S107, when an end signal indicating the end of observation of the subject is received from the outside via the antenna 27 and the transmitter/receiver 26 (Yes at Step S108), the capsule endoscope 2 ends this process. In contrast, when an end signal indicating the end of observation of the subject is not received from the outside via the antenna 27 and the transmitter/receiver 26 (No at Step S108), the capsule endoscope 2 returns to Step S101 described above.

In the following, at Step S101, a description will be given of a case in which an indication signal that indicates to perform white light observation is not received from the outside via the antenna 27 and the transmitter/receiver 26 (No at Step S101). In this case, the second illumination unit 22 radiates the particular light (Step S109). Then, the imaging unit 24 captures an image of the area irradiated with the particular light (Step S110).

Subsequently, the imaging unit 24 performs the read process of reading the image signal from each of the pixels in the image sensor 242 (Step S111).

Thereafter, the A/D converter 251 performs the A/D conversion process on the image signals that are read from the image sensor 242 (Step S112).

Subsequently, the gradation converter 252 performs the particular light gradation conversion process on the digital image signals input from the A/D converter 251 so as to be predetermined gradation (Step S113). Then, the transmitter/receiver 26 transmits the image signals that have been subjected to the gradation conversion by the gradation converter 252 to the outside (Step S114). After the process at Step S114, the capsule endoscope 2 advances the process to Step S108 described above.

Figures 6A, 6B, 6C:
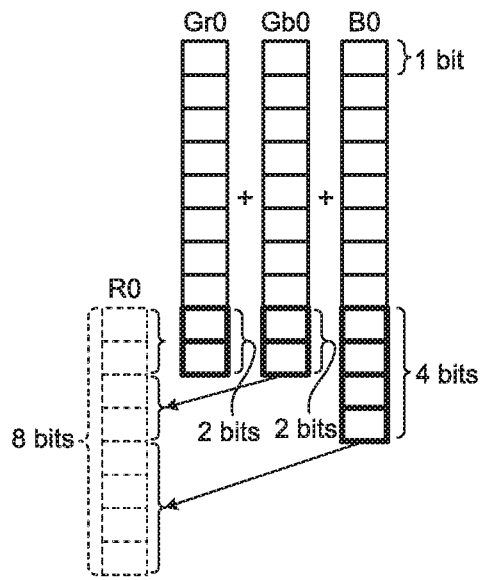
FIG. 6A is a diagram schematically illustrating the number of bits of a digital image signal obtained by each of the pixels before a particular light gradation conversion process is performed by the gradation converter in the capsule endoscope according to the first embodiment of the present disclosure.
FIG. 6B is a diagram schematically illustrating the number of bits of a digital image signal obtained by each of the pixels after the particular light gradation conversion process is performed by the gradation converter in the capsule endoscope according to the first embodiment of the present disclosure.
FIG. 6C is a diagram schematically illustrating allocation of bits of a digital image signal obtained by each of the pixels in the capsule endoscope according to the first embodiment of the present disclosure.

FIG. 6A is a diagram schematically illustrating the number of bits of a digital image signal obtained by each of the pixels before the particular light gradation conversion process is performed by the gradation converter 252. FIG. 6B is a diagram schematically illustrating the number of bits of a digital image signal obtained by each of the pixels after the particular light gradation conversion process is performed by the gradation converter 252. FIG. 6C is a diagram schematically illustrating allocation of bits of digital image signals. Incidentally, in FIG. 6C, 1 bit is schematically represented in a rectangular shape.

As illustrated in FIGS. 6A and 6B, regarding the digital image signals input from the A/D converter 251, the gradation converter 252 performs the particular light gradation conversion process of allocating a part of the image signal of the pixel having sensitivity to the particular light to a data area which has been allocated to the image signal generated by the pixel that does not have sensitivity to the particular light, and then outputs the processed digital image signals. Specifically, when the second illumination unit 22 radiates narrow band light included in either or both of the blue and green wavelength bands as particular light, the gradation converter 252 allocates a part of the image signals generated by the Gr pixel, the Gb pixel, and the B pixel to the third data area, which has been allocated to the third image signal generated by the R pixel that does not have sensitivity to the narrow band light, and then outputs the image signals. For example, when the B pixel, the Gr pixel, and the Gb pixel have received the particular light, the gradation converter 252 allocates, to the first data area allocated to the first image signal, an amount of data of the higher order 8 bits, out of 12 bits in the first image signal output from the B pixel, that is the same amount of data as that in the first data area allocated to the first image signal and allocating, to the third data area allocated to the third image signal, an amount of data of the lower order 4 bits that is the remaining amount of data of the first image signal, and then outputs the processed image signals to the transmitting/receiving unit 26. Furthermore, the gradation converter 252 allocates, to the second data area, an amount of data of 8 bits of the higher order bits, out of 12 bits in each of the second image signals output from the Gr pixel and the Gb pixel, that is the same amount of data as that in the second data area allocated to the second image signal and allocating, to the third data area allocated to the third image signal, an amount of data of the lower order 4 bits that is the remaining amount of data of the second image signal (regarding the Gr pixel and the Gb pixel, amount of data the lower order 2 bits), and then outputs the processed image signals to the transmitting/receiving unit 26 (from FIG. 6A to FIG. 6B). Then, as illustrated in FIG. 6C, the transmitting/receiving unit 26 sequentially transmits, to the transmitting/receiving unit 26, the image signals of each of the pixels (the R pixel, the Gr pixel, the Gb pixel, and the B pixel) that have been subjected to the allocation and the gradation conversion to 8 bits by the gradation converter 252. Namely, the transmitting/receiving unit 26 sequentially transmits data of 10 bits in the image signal of the Gr pixel, 10 bits in the image signal of the Gb pixel, and the 12 bits in the image signal of the B pixel. Consequently, even if the capsule endoscope 2 performs the particular light observation, it is possible to improve gradation of each of the G pixel and the B pixel without increasing an amount of data of image data.

According to the first embodiment of the present disclosure described above, when the B pixel, the Gr pixel, and the Gb pixel receive the particular light included in either or both of the blue and green wavelength bands radiated from the second illumination unit 22, because the data processing unit 25 allocates at least a part of one of the first image signal and the second image signal to the third image signal and outputs the image signal to the transmitting/receiving unit 26, even when particular light is observed, it is possible to generate a high gradation particular light image without increasing an amount of data.

Furthermore, according to the first embodiment of the present disclosure, when the B pixel, the Gr pixel, and the Gb pixel receive the particular light included in either or both of the blue and green wavelength bands radiated from the second illumination unit 22, because the gradation converter 252 allocates, to the first data area of the first image signal, a part of the first image signal output from the B pixel and allocating the rest of the first image signal to third data area of the third image signal that has been allocated to the third image signal output from the R pixel that does not have sensitivity to the particular light; allocates, to the second data area of the second image signal, a part of the second image signals output from the Gr pixel and the Gb pixel and allocating the rest of the second image signals to the third data area of the third image signal that has been allocated to the third image signal output from the R pixel that does not have sensitivity to the particular light; and outputs the image signals to the transmitting/receiving unit 26, even when the particular light is observed, it is possible to generate a high gradation particular light image without increasing an amount of data.

Furthermore, according to the first embodiment of the present disclosure, when the B pixel, the Gr pixel, and the Gb pixel receive the particular light included in either or both of the blue and green wavelength bands radiated from the second illumination unit 22, because the gradation converter 252 allocates, to the first data area of the first image signal, an amount of data of the higher order 8 bits, out of 12 bits in the first image signal output from the B pixel, that is the same amount of data as that in the first data area allocated to the first image signal and allocating, to the third data area allocated to the third image signal, an amount of data of the lower order 4 bits that is the remaining amount of data of the first image signal; allocates, to the second data area, an amount of data of 8 bits of the higher order bits, out of each of the 12 bits in the second image signal output from each of the Gr pixel and the Gb pixel, that is the same amount of data as that in the second data area allocated to the second image signal and allocating, to the third data area allocated to the third image signal, an amount of data of the lower order 4 bits that is the remaining amount of data of the second image signal (regarding the Gr pixel and the Gb pixel, an amount of data of the lower order 2 bits); and outputs the processed image signals to the transmitting/receiving unit 26, even when the particular light is observed, it is possible to generate a high gradation special light image without increasing an amount of data.

Incidentally, in the first embodiment according to the present disclosure, the gradation converter 252 allocates, to the third data area allocated to the third image signal output from the R pixel, an amount of data of the lower order 2 bits of the image signal of the Gr pixel and the Gb pixel and allocating an amount of data of the lower order 4 bits of the image signal of the B pixel; however, the gradation converter 252 may also allocate only an amount of data of 2 bits out of 12 bits in the image signal of the B pixel. Even with this, it is possible to improve gradation of each of the G pixel and the B pixel and reduce an amount of data at the time of transmission.

Second Embodiment

In the following, a second embodiment according to the present disclosure will be described. The second embodiment has the same configuration as that of the capsule endoscope system 1 according to the first embodiment described above and performs a process that is different from that performed by the capsule endoscope 2. Specifically, in the second embodiment, when the capsule endoscope performs a particular light observation, the capsule endoscope reads a signal from only pixels having sensitivity to the particular light. In a description below, the process performed by the capsule endoscope according to the second embodiment will be described. Furthermore, components that are identical to those in the capsule endoscope system 1 according to the first embodiment described above are assigned the same reference numerals and descriptions thereof will be omitted.

Process performed by the capsule endoscope FIG. 7 is a flowchart illustrating an outline of a process performed by a capsule endoscope according to a second embodiment of the present disclosure. In FIG. 7, Steps S201 to S210 correspond to Steps S101 to S110, respectively, illustrated in FIG. 4 described above.

Figure 8:
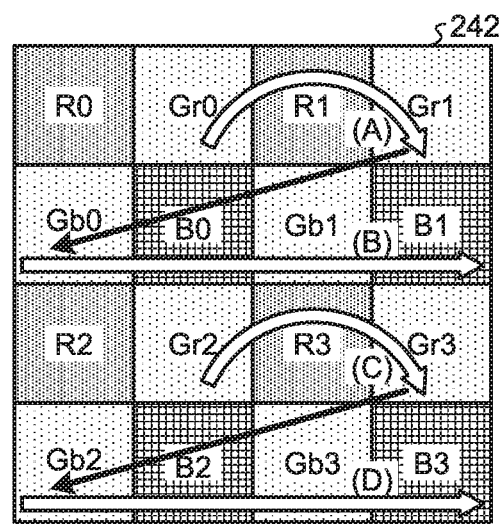
FIG. 8 is a diagram schematically illustrating an outline of a particular light read process performed by an imaging unit in the capsule endoscope according to the second embodiment of the present disclosure.

At Step S211, the imaging unit 24 performs a particular light read process of reading, from the image sensor 242, an image signal from only the pixels having sensitivity to the particular light. Specifically, as illustrated in FIG. 8, a narrow band light of NBI is irradiated as the particular light, because the R pixel does not have sensitivity to the narrow band light, the imaging unit 24 reads image signals from only the Gr pixel, the Gb pixel, and the B pixel that have sensitivity to the narrow band light and outputs the image signals to the A/D converter 251. In this case, the imaging unit 24 resets the pixel value of the R pixel.

Subsequently, the A/D converter 251 performs the A/D conversion process on the analog image signals that have been read from the image sensor 242 (Step S212).

FIG. 9A is a diagram schematically illustrating the number of bits of each of the pixels associated with the image signals that are present after the A/D conversion process performed by the A/D converter 251.

As illustrated in FIG. 9A, the A/D converter 251 performs the A/D conversion process of converting the analog image signals, which have been output from only the pixels having sensitivity to the particular light and that are included in the image sensor 242, to the digital image signals. Specifically, the A/D converter 251 performs the A/D conversion process of converting the analog image signals output from only the Gr pixel, the Gb pixel, and the B pixel to the digital image signals. Consequently, the image signal associated with each of the pixels having sensitivity to the particular light is converted to the digital image signal with the predetermined number of bits, for example, 12 bits.

After the process at Step S212, the gradation converter 252 performs the particular light gradation conversion process on the digital image signals input from the A/D converter 251 so as to be predetermined gradation (Step S213).

FIG. 9B is a diagram schematically illustrating the number of bits of each of the pixels associated with the image signals obtained after the special light gradation conversion process performed by the gradation converter 252.

As illustrated in FIG. 9B, the gradation converter 252 performs the special light gradation conversion process on the digital image signals output from only the pixel having sensitivity to the particular light and that is input from the A/D converter 251. Specifically, the gradation converter 252 outputs directly the first image signal, which has been output from the B pixel, without converting an amount of data of 12 bits, to the transmitting/receiving unit 26; converts an amount of data of 12 bits in the second image signal output from each of the Gr pixel and the Gb pixel to an amount of data of the higher order 10 bits; and outputs the image signal to the transmitting/receiving unit 26 (from FIG. 9A to FIG. 9B). More specifically, the gradation converter 252 allocates an amount of data of the lower order 4 bits (regarding the Gr pixel and the Gb pixel, an amount of data of the lower order 2 bits), out of each of the 12 bits in the first image signal and the second image signal, to the third data area that has been blank because the controller 29 does not read an image signal from the R pixel. Furthermore, the gradation converter 252 allocates, to the first data area of the first image signal and the second image data of the second image signal, an amount of data of the higher order 8 bits out of each of the 12 bits in the first image signal and the second image signal. Consequently, the gradation converter 252 can output directly the first image signal, which has been output from the B pixel, without converting an amount of data of 12 bits, to the transmitting/receiving unit 26; convert an amount of data of 12 bits in the second image signal output from each of the Gr pixel and the Gb pixel to an amount of data of the higher order 10 bits; and output the processed image signals to the transmitting/receiving unit 26. Consequently, it is possible to output the image signal with the same amount of data as that obtained in the case of white light described above in the first embodiment (see FIG. 5C) to the transmitting/receiving unit 26. Namely, even if the capsule endoscope 2 performs the particular light observation, it is possible to improve gradation of each of the G pixel and the B pixel without increasing an amount of data of the image data.

After the process at Step S213, the transmitting/receiving unit 26 transmits the image signal that has been subjected to the special light gradation conversion process performed by the gradation converter 252 to the outside (Step S214). After the process at Step S214, the capsule endoscope 2 advances the process to Step S208.

According to the second embodiment of the present disclosure described above, because the controller 29 reads an image signal from only the pixels having sensitivity to the particular light and outputs the image signal to the A/D converter 251, it is possible to reduce an amount of data processed by the A/D converter 251 and thus suppress the electrical power consumed in the capsule endoscope 2.

Furthermore, according to the second embodiment of the present disclosure, even when white light and particular light is used, it is possible to generate a high gradation special light image and output the image to the outside.

Incidentally, in the second embodiment according to the present disclosure, the gradation converter 252 outputs, to the transmitting/receiving unit 26, the second image signals, which have been output from the Gr pixel and the Gb pixel, with 10 bits, and the first image signal, which has been output form the B pixel, with 12 bits; however, as illustrated in FIG. 10, the gradation converter 252 may also output, to the transmitting/receiving unit 26, the first image signal, which has been output from the B pixel, with 10 bits. Consequently, it is possible to improve gradation of each of the G pixel and the B pixel and also it is possible to reduce an amount of data at the time of transmission.

OTHER EMBODIMENTS

The present disclosure is not limited to the embodiments described above and various modifications and applications are, of course, possible as long as they do not depart from the spirit of the present disclosure. For example, in addition to the capsule endoscope used for explanation of the present disclosure, the present disclosure is applicable for an endoscope apparatus (flexible endoscope), a nasal endoscope apparatus, a rigid endoscope, an imaging apparatus, a medical device, and an industrial endoscope formed by arranging an imaging unit at a distal end portion of an insertion portion to be inserted into a subject.

Furthermore, the above embodiments according to the present disclosure are described with the color filter of a Bayer arrangement; however, the array of the color filter is not limited to this and a known filter with different arrangements may also be used.

Furthermore, in the embodiments according to the present disclosure, the particular light is exemplified to include light in a blue narrow band (for example, 390 nm to 445 nm) and/or light in a green narrow band (for example, 530 nm to 550 nm); however, the embodiment is not limited to this. When the capsule endoscope performs a fluorescence observation (autofluorescence imaging: AFI), light including light in a wavelength band (for example, 390 nm to 470 nm) that is used for the autofluorescence observation irradiating a fluorescent material and light in a wavelength band (for example 540 nm to 560 nm) that is absorbed by hemoglobin in the blood may also be used as the particular light. Furthermore, when the capsule endoscope performs a narrow band light observation (dual red imaging: DRI) that observes a mucous membrane of the digestive tract and a lower layer of a mucous membrane, the particular light may include light and additional light both of which are in a red narrow band (for example, the light of 600 nm and the additional light of 630 nm). Furthermore, when the capsule endoscope performs an infrared light observation (Infra-Red Imaging: IRI), the particular light may include an infrared light and additional infrared light both of which are in an infrared wavelength band (for example, 790 nm to 820 nm and 905 nm to 970 nm). In these cases, a color filter suitable for observation may be arranged on the light-receiving surface of the image sensor.

Furthermore, in the explanation of each operation flowchart described above in this document, the operations are described using "first", "then", "subsequently", "thereafter", and the like; however, this does not mean that it is necessary to perform the operations in this order.

Furthermore, the technique of each of the processes performed by the capsule endoscope according to the embodiment described above, i.e., the process indicated by each of the flowcharts, may be stored as programs executed by a controller, such as a CPU. Furthermore, the process may also be stored in a storage medium of an external storage device, such as a memory card (a ROM card, a RAM card, or the like), a magnetic disk, a hard disk, an optical disk (a CD-ROM, a DVD, or the like), or a semiconductor memory, and then distributed. Then, the controller, such as a CPU, reads the program stored in the storage medium of the external storage device and the operations are controlled by the read program, thereby the processes described above can be executed.

Furthermore, the present disclosure is not limited to the above described embodiments and modifications as they are. In the implementation stage, the present disclosure may be embodied with various modifications of components as long as they do not depart from the scope of the disclosure. In addition, various embodiments may be made by appropriately combining a plurality of components disclosed in the above embodiments. For example, some components may be deleted from all of the components described in the embodiments and the modifications described above. Furthermore, the components described in the embodiments and the modifications may be appropriately combined.

According to the present disclosure, an advantage is provided in that, even when special light is irradiated, it is possible to generate a high gradation special light image without increasing an amount of data.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A body-insertable apparatus comprising:
an image sensor including
a first pixel configured to receive light of a first wavelength band and to generate a first image signal,
a second pixel configured to receive light of a second wavelength band that is different from the first wavelength band and to generate a second image signal, and
a third pixel configured to receive a third wavelength band that is different from the first wavelength band and the second wavelength band and to generate a third image signal; and
a processor comprising hardware, wherein the processor is configured to:
when first light is received on the first pixel and the second pixel, the first light including at least one of the light of the first wavelength band and the light of the second wavelength band and excluding the light of the third wavelength band,
allocate a part of the first image signal to a first data area of the first image signal,
allocate the rest of the first image signal to a third data area of the third image signal,
allocate a part of the second image signal to a second data area of the second image signal,
allocate at least one of the rest of the first image signal and the rest of the second image signal to the third data area of the third image signal, and
transmit the third image signal including the at least one of the rest of the first image signal and the rest of the second image signal.

2. The body-insertable apparatus according to claim 1, further comprising a transmitter configured to transmit the first image signal, the second image signal, and the third image signal that are obtained by the allocation due to the processor.

3. The body-insertable apparatus according to claim 2, wherein the transmitter transmits the first image signal, the second image signal, and the third image signal from the processor, to the outside.

4. The body-insertable apparatus according to claim 1, wherein
amounts of data in the first, the second, and the third data areas are smaller than amounts of data of the first, the second, and the third image signals, respectively, and
when the first light is received on the first pixel and the second pixel, the processor allocates
the same amount of data as the amount of data of the first data area of the first image signal to the first data area,
at least a part of the remaining amount of data of the first image signal to the third data area,
the same amount of data as the amount of data of the second data area of the second image signal to the second data area, and
at least a part of the remaining amount of data of the second image signal to the third data area.

5. The body-insertable apparatus according to claim 1, wherein when second light is received on the first pixel, the second pixel, and the third pixel, the second light including the first wavelength band, the second wavelength band, and the third wavelength band, the processor is further configured to convert the first image signal, the second image signal, and the third image signal to a predetermined amount of data.

6. The body-insertable apparatus according to claim 1, wherein the processor is further configured to allow only the first image signal and the second image signal to be output from the image sensor when the first light is received on the first pixel and the second pixel.

7. The body-insertable apparatus according to claim 1, further comprising:
a first illumination device configured to emit the first light; and
a second illumination device configured to emit the second light.

8. The body-insertable apparatus according to claim 1, wherein
the first wavelength band is a blue wavelength band,
the second wavelength band is a green wavelength band,
the third wavelength band is a red wavelength band, and
the first light includes at least one of a first narrow band being within and narrower than the blue wavelength band, and a second narrow band being within and narrower than the green wavelength band.

9. The body-insertable apparatus according to claim 8, wherein the first narrow band is 390 nm to 445 nm, and
the second narrow band is 530 nm to 550 nm.

10. The body-insertable apparatus according to claim 1, wherein the processor is configured to allocate the same amount of data as the amount of data of the first data area of the first image signal to the first data area,
allocate the remaining amount of data of the first image signal to the third data area,
allocate the same amount of data as the amount of data of the second data area of the second image signal to the second data area, and
allocate the remaining amount of data of the second image signal to the third data area.

11. A transmission method comprising:

when first light is received on a first pixel configured to receive light of a first wavelength band and to generate a first image signal and a second pixel configured to receive light of a second wavelength band that is different from the first wavelength band and to generate a second image signal, the first light including at least one of the light of the first wavelength band and the light of the second wavelength band and excluding light of a third wavelength band that is different from the first wavelength band and the second wavelength band,
allocating a part of the first image signal to a first data area of the first image signal,
allocating the rest of the first image signal to a third data area of a third image signal of a third pixel configured to receive light of the third wavelength band to generate the third image signal,
allocating a part of the second image signal to a second data area of the second image signal,
allocating the rest of the second image signal to the third data area of the third image signal, and
transmitting the third image signal including the rest of the first image signal and the rest of the second image signal.

12. A non-transitory computer readable medium storing a program that causes a body-insertable apparatus to execute a process comprising:

when first light is received on a first pixel configured to receive light of a first wavelength band and to generate a first image signal and a second pixel configured to receive light of a second wavelength band that is different from the first wavelength band and to generate a second image signal, the first light including at least one of the light of the first wavelength band and the light of the second wavelength band and excluding light of a third wavelength band that is different from the first wavelength band and the second wavelength band,
allocating a part of the first image signal to a first data area of the first image signal,
allocating the rest of the first image signal to a third data area of a third image signal of a third pixel configured to receive light of the third wavelength band to generate the third image signal,
allocating a part of the second image signal to a second data area of the second image signal,
allocating the rest of the second image signal to the third data area of the third image signal, and
transmitting the third image signal including the rest of the first image signal and the rest of the second image signal.

* * * * *